(12) United States Patent
Kazanovicz

(10) Patent No.: US 10,322,002 B2
(45) Date of Patent: Jun. 18, 2019

(54) VETERINARY HIP RESURFACING PROSTHETIC SYSTEM

(71) Applicant: MWI Veterinary Supply Co., Boise, ID (US)

(72) Inventor: Andrew J. Kazanovicz, Holland, MA (US)

(73) Assignee: MWI Veterinary Supply Co., Boise, ID (US)

( * ) Notice: Subject to any disclaimer, the term of this patent is extended or adjusted under 35 U.S.C. 154(b) by 64 days.

(21) Appl. No.: 15/611,071

(22) Filed: Jun. 1, 2017

(65) Prior Publication Data

US 2017/0367830 A1 Dec. 28, 2017

Related U.S. Application Data

(60) Provisional application No. 62/355,479, filed on Jun. 28, 2016.

(51) Int. Cl.
| | | |
|---|---|---|
| *A61F 2/34* | (2006.01) | |
| *A61F 2/36* | (2006.01) | |
| *A61F 2/30* | (2006.01) | |
| *A61F 2/46* | (2006.01) | |

(52) U.S. Cl.
CPC ............ *A61F 2/34* (2013.01); *A61F 2/36* (2013.01); *A61F 2/3603* (2013.01); *A61F 2002/307* (2013.01); *A61F 2002/3411* (2013.01); *A61F 2002/4641* (2013.01)

(58) Field of Classification Search
CPC ............. A61F 2002/30495; A61F 2002/30611
See application file for complete search history.

(56) References Cited

U.S. PATENT DOCUMENTS

| 4,715,860 A | 12/1987 | Amstutz et al. | |
|---|---|---|---|
| 6,497,727 B1 | 12/2002 | Pope et al. | |
| 7,169,185 B2 | 1/2007 | Sidebotham | |
| 7,858,671 B2 | 12/2010 | Merrill et al. | |
| 8,728,464 B2 | 5/2014 | Haas | |
| 2006/0217814 A1* | 9/2006 | Lambert | A61F 2/32 623/22.17 |
| 2008/0009951 A1 | 1/2008 | Hodge | |
| 2010/0049329 A1 | 2/2010 | Vio | |
| 2010/0174380 A1* | 7/2010 | Lewis | A61F 2/32 623/22.11 |
| 2010/0191344 A1 | 7/2010 | Grundel et al. | |

(Continued)

OTHER PUBLICATIONS

BioMedtrix, 50 Intervale Road, Suite 5, Boonton, NJ 07005, "Universal Hip Catalog & Information", www.biomedtrix.com, Apr. 13, 2017, 13 pages.

(Continued)

*Primary Examiner* — Jason-Dennis N Stewart
(74) *Attorney, Agent, or Firm* — Iandiorio Teska & Coleman, LLP

(57) ABSTRACT

A veterinary hip resurfacing prosthetic system includes a femoral cap and an acetabular cup. The cup shell has a thickness of less than 2 mm and a liner in the shell has a thickness of less than 2.5 mm in order to accommodate a larger femoral cap. Further included are features for preventing rotation of the liner relative to the shell, for releasably locking the liner in the shell, and for accessing the liner to remove it from the shell.

15 Claims, 5 Drawing Sheets

(56) References Cited

U.S. PATENT DOCUMENTS

| | | | |
|---|---|---|---|
| 2012/0141429 A1* | 6/2012 | Hass | A61L 27/3821 |
| | | | 424/93.7 |
| 2013/0073050 A1* | 3/2013 | McEntire | A61F 2/32 |
| | | | 623/22.11 |
| 2013/0297036 A1* | 11/2013 | Collins | A61F 2/34 |
| | | | 623/22.24 |
| 2014/0303742 A1* | 10/2014 | Prybyla | A61F 2/34 |
| | | | 623/22.19 |
| 2015/0335437 A1 | 11/2015 | Bruun Lauritzen et al. | |
| 2016/0015520 A1* | 1/2016 | Smith | A61F 2/34 |
| | | | 623/22.19 |

OTHER PUBLICATIONS

Hospital for Special Surgery, "Hip Resurfacing: An Overview" Richard S. Laskin, MD, May 22, 2006, 11 pages.

MJ3 Industries, LLC, P.O. Box 105, Cataldo, ID, "Pilot Animal Study, Improving orthopedics through nanotechnology", Institutional Animal Care and use Committee (IACUC), fall of 2012, 6 pages.

Haas et al., "Synthetic Osteogenic Extracellular Matrix Formed by Coated Silicon Dioxide Nanosprings", Journal of Nanobiotechnology, 2012, 10:6, 12 pages.

BoneSmart, What is the difference between hip resurfacing and total hip replacement?, http://bonesmart.org/hip/what-is-the-difference-between-hip-resurfacing-and-total-hip-replacement/, 3 pages.

Written Opinion of the International Searching Authority for International Application No. PCT/US2017/035476, dated Aug. 14, 2017, five (5) pages.

\* cited by examiner

VETERINARY HIP RESURFACING PROSTHETIC SYSTEM

RELATED APPLICATIONS

This application claims benefit of and priority to U.S. Provisional Application Ser. No. 62/355,479 filed Jun. 28, 2016, under 35 U.S.C. §§ 119, 120, 363, 365, and 37 C.F.R. § 1.55 and § 1.78, which is incorporated herein by this reference.

FIELD OF THE INVENTION

This subject invention relates to veterinary hip resurfacing surgeries.

BACKGROUND OF THE INVENTION

In humans, total hip replacement, partial hip replacement, and hip resurfacing prosthetic devices and surgeries are common. See U.S. Published Patent Application No. 2008/0009951 incorporated herein by this reference.

In dogs, total hip replacement surgeries are used, for example, to correct hip dysplasia. For veterinary uses, hip replacement prosthetics and surgical methods are quite different from those used on humans. See U.S. Pat. No. 7,169,185 incorporated herein by this reference.

Currently, in veterinary medicine, total hip prosthetic devices and total hip replacement surgeries are used where the upper part of the femur is replaced with a stem device including a prosthetic head or ball. An acetabular cup is fit into the hip socket and receives the prosthetic head or ball therein. See U.S. Pat. No. 7,169,185 incorporated herein by this reference.

Canine hip resurfacing prosthetic components and surgeries are not currently available but would be advantageous for certain cases since the upper part of the femur is not removed. Hip resurfacing prosthetic components and surgeries for canines may be useful, for example, for younger, active dogs. A femoral cap and lined acetabular cup has been proposed. See U.S. Published Patent Application No. 2010/0049329 incorporated herein by this reference. The liner of the acetabular cup is hot assembled into the shell of the acetabular cup and both the liner and the shell are relatively thick.

BRIEF SUMMARY OF THE INVENTION

The typical liner of a veterinary use acetabular cup is made thick because it wears. Such a thick liner limits the size of the femoral cap that may be used resulting in the removal of more femoral head/ball bone material than may be necessary, potentially resulting in femoral neck fracture (in hip resurfacing) due to insufficient bone stock, or hip dislocation (in total hip replacement) due to a relatively smaller femoral head size.

Metal on metal prosthetics where the acetabular cup has no liner may be disadvantageous and/or may be perceived to be disadvantageous due to metallic wear debris ions which can cause metallosis.

Featured, in some embodiments, are prosthetic components for veterinary (e.g., canine) use in which the acetabular cup shell and liner are both thin accommodating a larger femoral cap, in which the material of the acetabular cup liner is highly wear resistant and in which the liner is replaceable. At the same time, the liner is prevented from moving inside the acetabular cup shell. Various means are disclosed for securing the acetabular cup in the hip socket.

The subject invention, however, in other embodiments, need not achieve all these objectives and the claims hereof should not be limited to structures or methods capable of achieving these objectives.

Featured is a veterinary hip resurfacing prosthetic system comprising a femoral cap and an acetabular cup. The cup preferably includes a shell having a thickness of less than 2 mm, a liner in the shell having a thickness of less than 2.5 mm, means for preventing rotation of the liner relative to the shell, means for releasably locking the liner in the shell, and means for accessing the liner to remove it from the shell.

In one example, the cup shell is approximately 1.0 mm thick and the cup liner is approximately 1.5 mm thick. The means for preventing rotation of the liner relative to the shell may include spaced pockets internal in the shell and corresponding spaced tabs exterior to the liner received in the shell pockets. The means for releasably locking may include a ring interior to the shell and groove exterior to the liner receiving the shell ring therein. The means for accessing the liner may include slots or castellations at the rim of the shell.

In some example, the acetabular cup shell has an exterior surface with nano-springs thereon. The liner is preferably made of highly cross-linked ultra-high molecular weight polyethylene. The femoral cap may include an inner surface with nano-springs thereon. In other examples, the femoral cap may include an exterior surface with a PVD coating thereon.

Also featured is a veterinary hip resurfacing prosthetic acetabular cup comprising a shell and a cross linked ultra-high molecular weight polymer liner having a thickness of less than 2.5 mm. The shell may have a thickness of less than 2.0 mm. Complementary features in the shell and liner preventing rotation of the liner relative to the shell. A ring internal to shell is received in a groove external to the liner for locking the liner in a shell.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
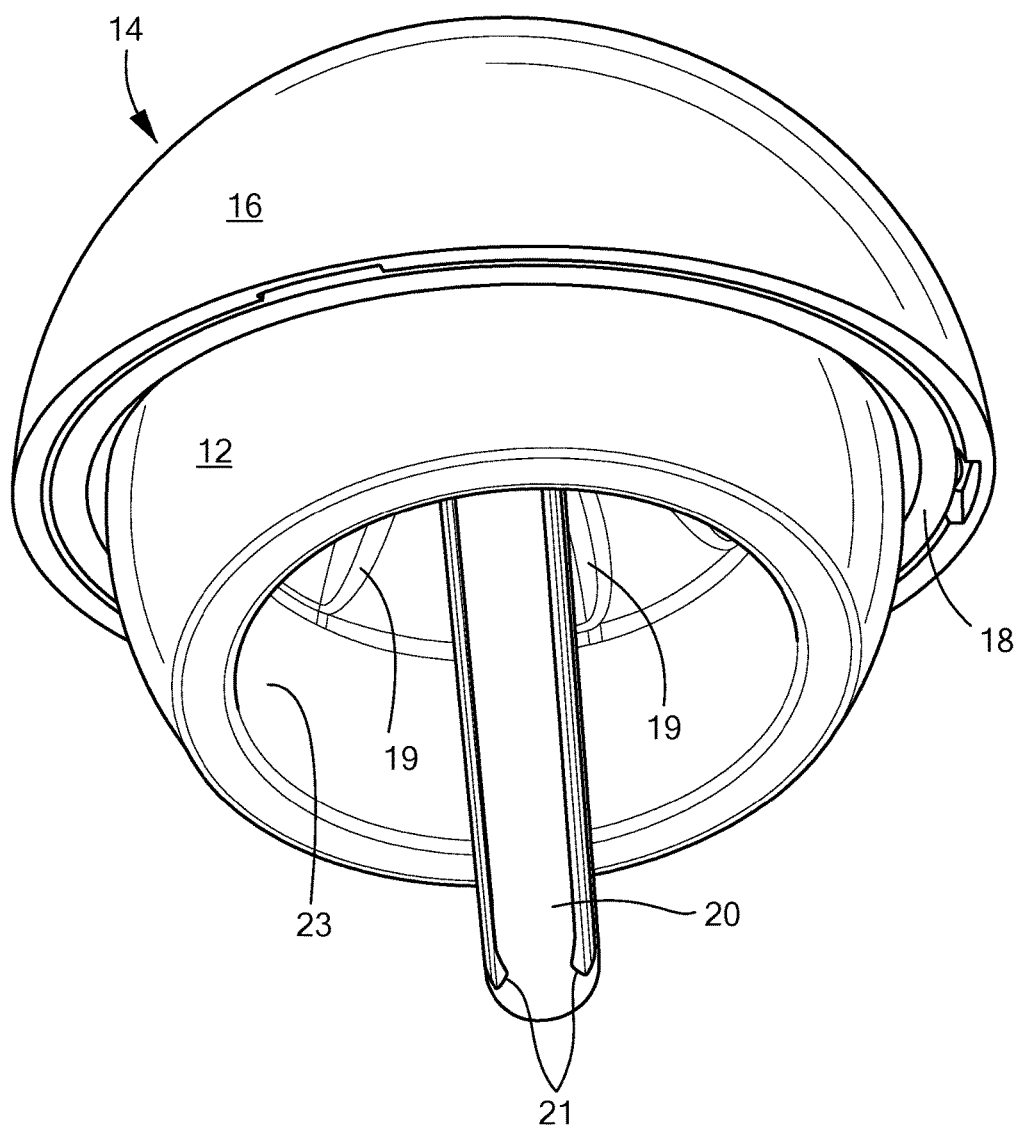
FIG. 1 is a schematic view showing an example of a femoral cap and acetabular cup useful in canine hip resurfacing surgeries.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows components of a canine hip resurfacing prosthesis including femoral cap 12 and acetabular cup 14 with shell 16 and liner 18. In this particular example, shell 16 may be made of titanium. Cobalt chromium and stainless steel are other options. Liner 18 may be made of highly cross-linked ultrahigh molecular weight polyethylene (UHMWPE). See U.S. Pat. No. 7,858,671 incorporated herein by this reference. Preferably, a highly cross linked UHMWPE liner is used and is very thin, for example, less than 2.5 mm thick and in one example 1.5 mm thick. Shell 16 may also be very thin, for example, less than 2 mm thick and in one example 1.0 mm thick. In testing, the liner material survived 1,100,000 load cycles without cracking, exhibiting a wear rate of 0.81 mg/1,000,000 cycles. Additionally, 3D imaging results indicated a maximum wear penetration of 0.15 mm, or ~10% of liner thickness.

Femoral cap 12 may be made of stainless steel. Cobalt chromium or titanium may also be used. Cap 12 preferably includes stem 20. Preferably, femoral cap 12 will include interior surface indentations 19, less than 1 mm deep, and in one example 0.5 mm deep. Stem 20 may also include indentations 21. These indentations can accommodate PMMA bone cement, in one example. Alternatively, femoral cap 12 inner surface 23 may accommodate titanium beads, a porous outer surface, cement-less press fit, or nano-springs, among others. In addition, the exterior surface of femoral cap 12 may include a low-friction, thin film physical vapor deposition (PVD) coating ordiamond like carbon (DLC) coating, such as titanium niobium nitride in one example. The PVD coating can be used to improve the surface properties (specifically wear) of the femoral cap 12 while simultaneously affording it an immune privileged state.

Preferably, the acetabular cup liner 18 is replaceable with respect to shell 16. Such a replaceable liner enables a worn liner to be replaceable without removing the acetabular cup shell from the hip. Also, if later in the dog's life a total hip replacement prosthetic head or ball is desired, a new acetabular cup liner which is designed to mate with the prosthetic head or ball can be inserted in the same in-place acetabular cup shell. Typically, the prosthetic ball used in a total hip replacement is smaller than the femoral cap used in a hip resurfacing so such a replaced liner would typically be thicker than 1.5 mm (for example, a liner with an inside diameter of 17 mm and a thickness of 2.4-6.4 mm). See U.S. Pat. No. 7,169,185 incorporated herein by this reference disclosing a liner which mates with a 17 mm prosthetic femoral ball. A replaceable liner is also useful given certain sterility shelf life issues associated with the liner. In inventory, when a liner exceeds its shelf life, another liner can be used in an acetabular cup shell. The liner may be snap fit into the acetabular cup shell. Other features associated with the shell and/or the liner may be used to removably lock the liner in the shell.

Various technologies may be used to adequately secure the outer surface of the acetabular cup shell to the hip socket and/or to secure the inner surface of the femoral cap to the resurfaced canine hip ball. Titanium beads may be used. See U.S. Pat. No. 7,169,185 incorporated herein by this reference. A porous outer surface may be used. See U.S. Pat. No. 4,715,860 incorporated herein by this reference. A cementless press fit of the acetabular cup into the hip socket may be preferable. However screws and/other fasteners may be used. Preferably, a Nano-spring Enhanced Osseointegration technique is used on the exterior of the acetabular cup shell. See U.S. Pat. No. 8,728,464 incorporated herein by this reference.

Other coatings include a hydroxyapatite (HA) coating on titanium, cobalt-chromium or stainless steel; titanium plasma spray (TPS) orthopedic coating on titanium or CoCr substrates with a purity that enables the coating to exceed the ASTM requirement thereby eliminating cracking; resorbable blast media (RBM) surface treatment on titanium substrates creating a roughened surface comparable to a 100 mesh Al2O3 finish without leaving any embedded debris; composite coatings including HA on plasma, beads, irregular sintered coatings and TPS on RBM-prepared substrates; porous coatings such as spherical beads, asymmetrical powder and irregular particle coatings, available in a range of powder sizes, types and coating processes to meet tight tolerances or unusual specifications; custom coating technologies including traditional bead coatings as well as more novel applications such as porous metal foams; a rough porous TPS coating with—higher roughness and greater porosity (>100 micron pore size in all zones) that meets the ASTM standard for porous coating; thin HA coatings with less than 5 microns thickness, which covers the entire surface of the implant, including the insides of the pore, which helps osseointegration.

In cemented versions, a PMMA coating placed over entire exterior surface of the acetabular cup shell, PMMA spacers placed into specific pockets in the exterior surface of the acetabular cup shell, PMMA coating placed over the entire interior surface of the acetabular cup shell and pressed through pores or holes which pass through to the exterior surface of the acetabular cup shell to affix to bone.

In cement-less versions porous coatings may be used. Also a trans acetabular screw: single or multi-screw fixation into bone, single or multi-taper posts which are impacted into bone or a flange with lip connecting to the acetabular cup shell edge that accepts screw for fixation into bone.

Any place where screws are used, Steinmann pins could be used instead. Additionally, a combination of these fixation methods could be used, for example a porous coating plus trans acetabular screws, or posts plus PMMA spacers and the like.

The femoral cap may also be fixed to the femoral head in the following methods: cemented, e.g., a PMMA coating placed over the entire interior surface of the femoral cap. Cement-less versions include porous coatings, an unthreaded post, a threaded post featuring a profile similar to cancellous bone screw, a craniodorsal screw (see U.S. Published Patent Application No. 2010-0049329), medial screws (see U.S. Published Patent Application No. 2008-0009951), and stemless versions (see U.S. Published Patent Application Nos. 2010-0191344 and 2015-0335437) all incorporated herein by this reference. A craniodorsal to caudoventral screw similar to U.S. Published Patent Application No. 2010-0049329, except passing through both bone cortices, may include a nut on caudoventral side to lock into place. Single or multi-taper posts emanating from interior surface of femoral cap 12 which can be impacted into bone and/or a flange which extends down the femoral neck, which accepts screws perpendicular to the axis of the femoral neck can be used.

Any place where screws are used, Steinmann pins could be used instead. Additionally, a combination of these fixation methods could be used such as threaded post plus porous coating or unthreaded post plus PMMA coating.

Figure 2:
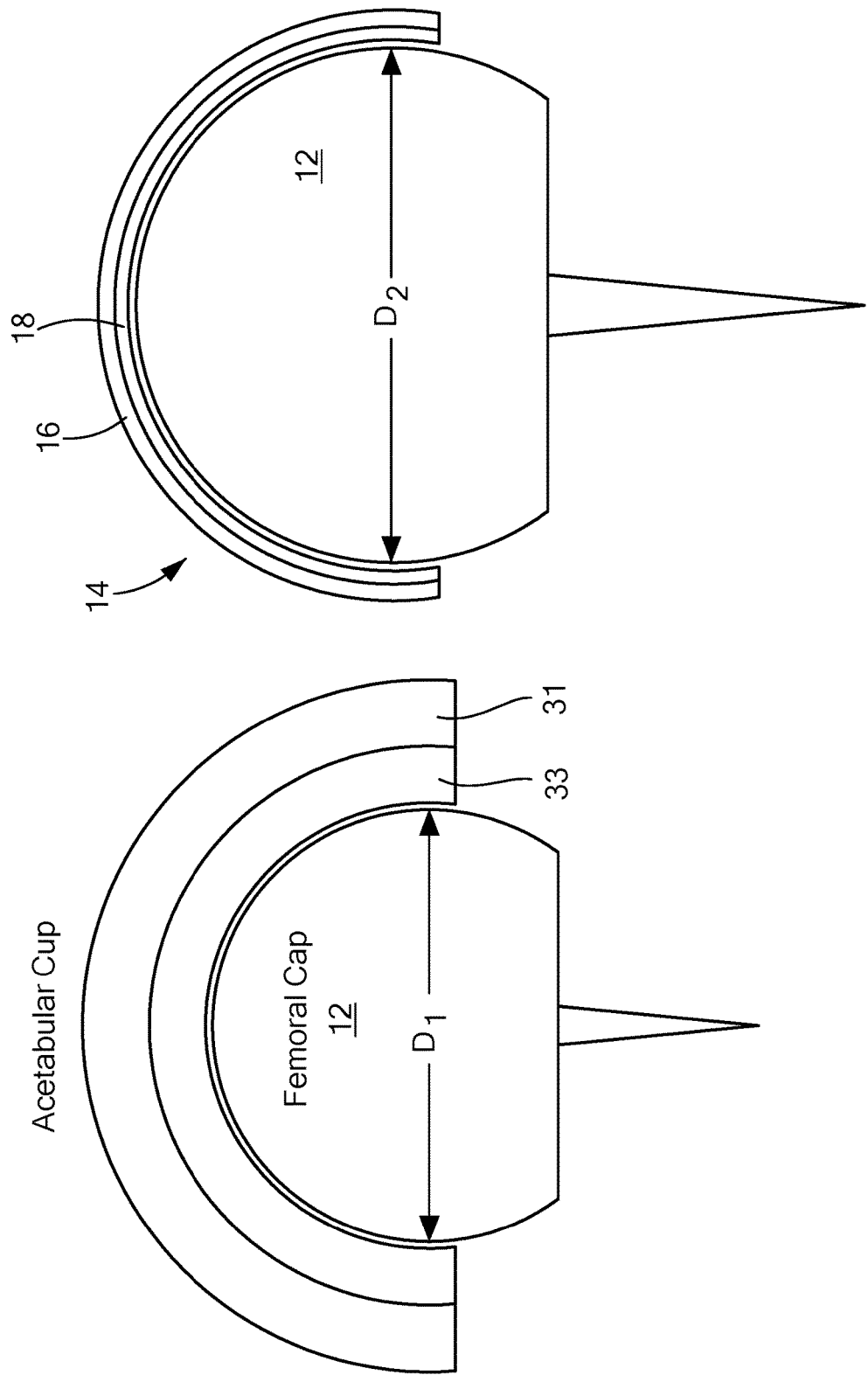
FIG. 2A is a schematic cross-sectional view showing a prior acetabular cup with a relatively thick shell and thick liner.
FIG. 2B is a schematic cross-sectional view showing an example of the invention where both the acetabular cup shell and liner are relatively thin thus accommodating a larger femoral cap.

As shown in FIG. 2A, a prior art canine acetabular cup had a relatively thick shell 31 and thick liner 33 resulting in a femoral cap with an outside diameter $D_1$. In the subject invention, the shell 16 and liner 18 are relatively thin allowing use with a femoral cap having a larger outside diameter $D_2$. The outside diameter of the acetabular cup shell in FIGS. 2A and 2B is the same (e.g., 26 mm). The result is less femoral ball material need be removed during surgery in the case of the design of FIG. 2B versus the design of FIG. 2A thus reducing the chance of hip dislocation due to the relatively larger femoral head size. And yet, thin liner 18, FIG. 2B, preferably made out of highly cross-linked ultra-high molecular weight polyethylene does not wear appreciably and preferably only wears at a rate of 1.0 mg/1,000,000 cycles or less.

Exemplary dimensions (in mm) for the femoral cap and acetabular cup and liner are disclosed in the table below.

TABLE 1

| | FEMORAL CAP | ACETABULAR CUP |
|---|---|---|
| Large Dog | 23 OD | 28 Shell OD |
| 65+ lbs. | 18 ID | 26 Shell ID |
| | | 23 Liner ID |
| | | 26 Liner OD |
| Medium Dog | 21 OD | 26 Shell OD |
| 30-65 lbs. | 16 ID | 24 Shell ID |
| | | 21 Liner ID |
| | | 24 Liner OD |
| Small Dog | 18 OD | 23 Shell OD |
| Less than 30 lbs. | 13 ID | 21 Shell ID |
| | | 18 Liner ID |
| | | 21 Liner OD |

The acetabular cup may include means to releasably lock the liner with respect to the shell. For example, in FIG. 3, liner 18 has, just below rim 30, a circumferential internal groove 36 between ridges 38a and 38b. Shell 16 has, just below rim 40, an interior circumferential beveled ring 41 which snap fits into groove 36 of liner 18. In testing, the liner/shell locking mechanism performed favorably and it took on average 647 newtons to push the liner out of the shell.

Figure 3:
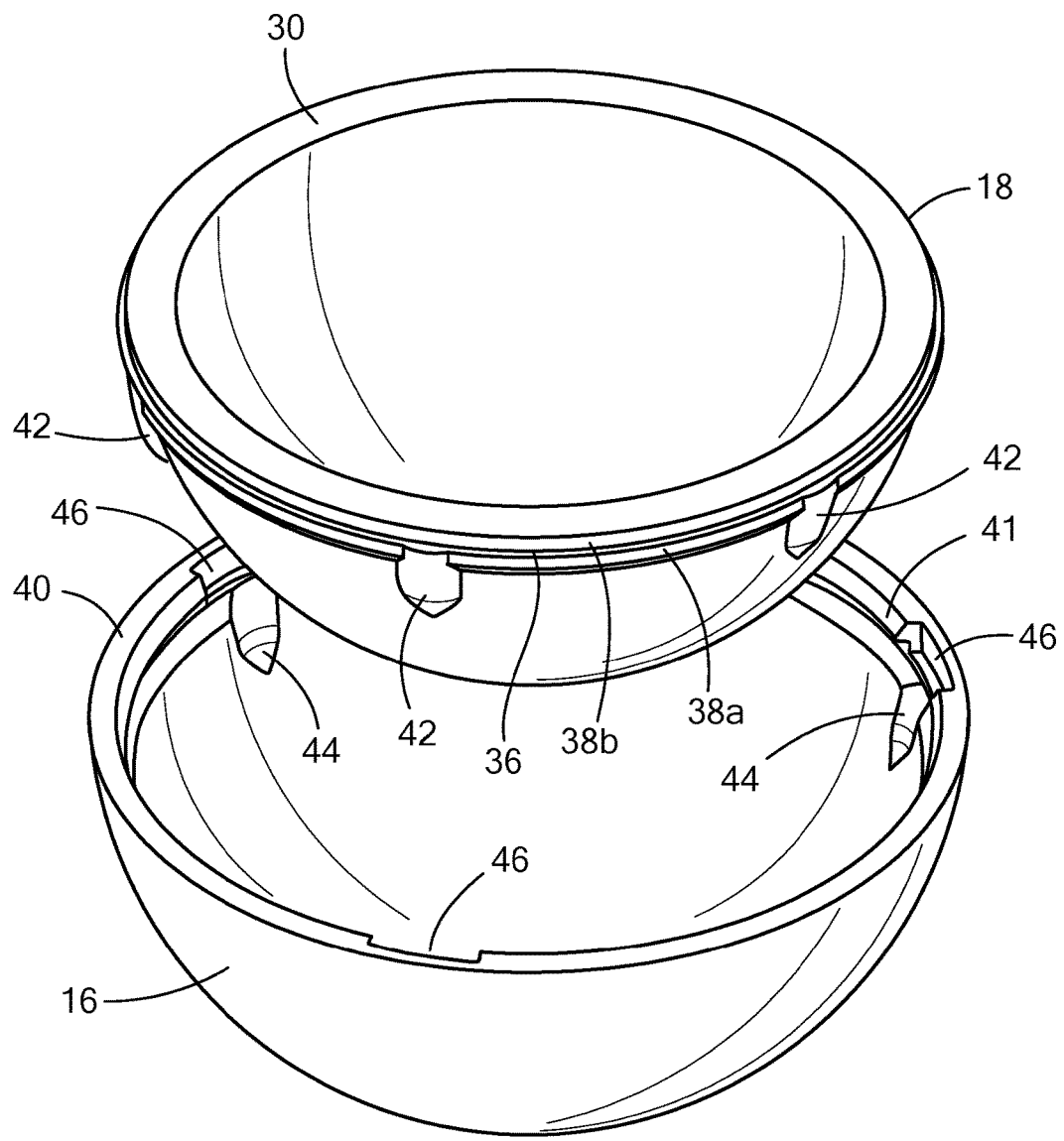
FIG. 3 is a schematic view showing an example of an acetabular cup liner and shell.

The acetabular cup may further include means for preventing rotation of the liner relative to the shell to prevent wear of the liner. In FIG. 3, the liner 18 has spaced exterior tabs 42 below rim 30 and shell 16 includes a corresponding set of spaced interior seats 44 for receiving the tabs of the liner therein to prevent rotation of the liner in the shell.

The acetabular cup may further include means for accessing the liner assisting in the removal of the liner from the shell. For example, in FIG. 3 shell 16 includes spaced liner removal slots 46 in the shell rim for a tool access enabling removal of the liner for the shell.

The liner is preferably made from a cross-linked ultra-high molecular weight polyethylene material. See U.S. Pat. No. 7,858,671. The liner may be compression molded or machined. The machined liner may be machined from a cross-linked, thermally annealed block of UHMWPE material. The machined liner may then be sterilized.

Figure 4:
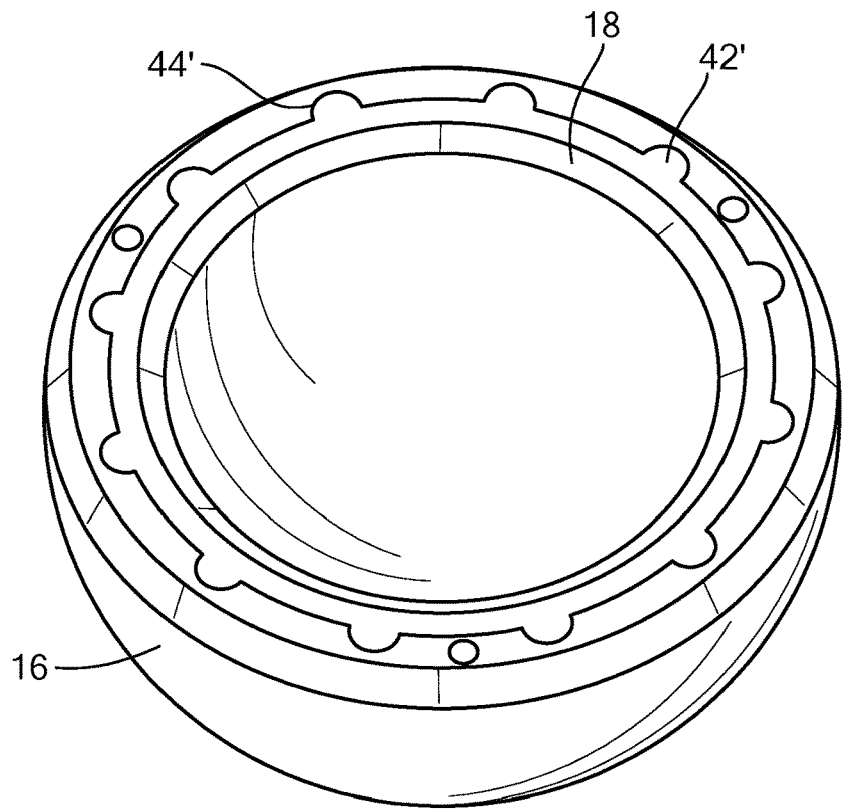
FIG. 4 is a schematic view showing another example of an acetabular cup.
Figure 5:
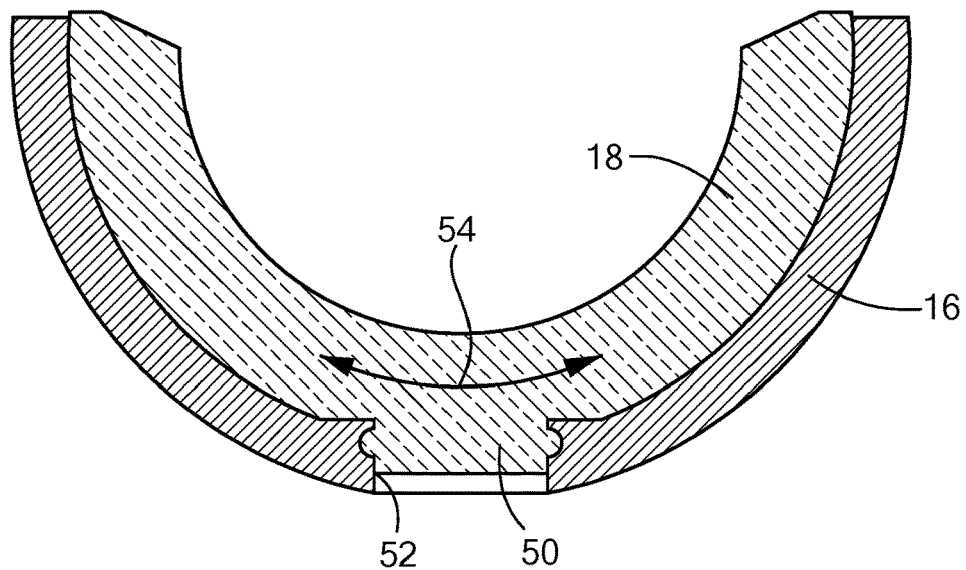
FIG. 5 is a schematic cross-sectional view showing still another example of an acetabular cup.

In another design, the liner 18, FIG. 4 had a plurality of (e.g., 12) anti-rotation tabs 42' at the rim of the liner received in seats 44' at the rim of shell 16. In FIG. 5, liner 18 included a positive exterior feature 50 at the apex of the liner snap fit into a recess 52 at the interior bottom of shell 16. These features prevent rotation of the liner in the direction shown by arrow 54.

Figure 6:
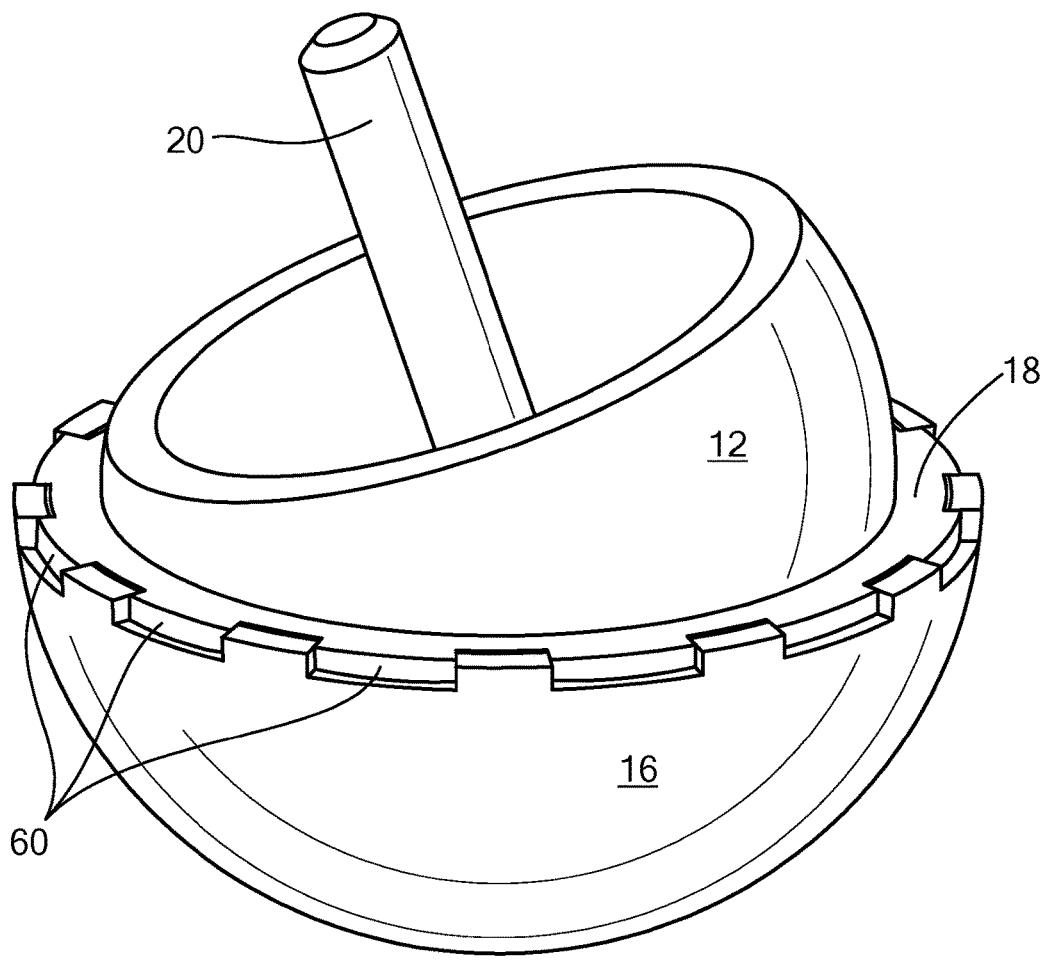
FIG. 6 is a schematic view showing an additional example of an acetabular cup liner and shell.

In FIG. 6, the liner removal assist features are castellations 60 in the rim of the shell 16.

In surgery, the canine hip ball is sculpted to accept the femoral cap 12, FIG. 1. The canine hip socket is sculpted to accept the acetabular cup 14 with the liner installed in the shell. The acetabular cup may be press fit into the sculpted hip socket.

Wear testing was performed on 8 hip liners made of highly cross-linked UHMWPE (24 mm dia, 75 kGy). Four liners served as a "soaking" control (axial load only), the other four were loaded using motions that simulated the gait of adult canines (axial+torsional load). The liners were loaded for 1,100,000 cycles. Each test consisted of four stages of 275,000 cycles. All of the liners survived without cracking. The wear rate was 0.81 mg/million cycles. Initial imaging results indicate a max wear penetration of 0.15 mm, or ~10% of liner thickness. An initial drop in mass was observed. This may be due to the high surface roughness of the femoral head (veterinary hip=0.77 μm, standard human hip=0.05 μm).

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A veterinary hip resurfacing prosthetic system comprising:
   a femoral cap; and
   an acetabular cup including:
      a shell having a thickness of less than 2 mm,
      a liner in the shell having a thickness of less than 2.5 mm,
      means for preventing rotation of the liner relative to the shell,
      means for releasably locking the liner in the shell, and
      means for accessing the liner to remove it from the shell.

2. The system of claim 1 in which the shell is approximately 1.0 mm thick and the liner is approximately 1.5 mm thick.

3. The system of claim 1 in which the means for preventing rotation of the liner relative to the shell includes spaced seats internal in the shell and corresponding spaced tabs exterior to the liner received in said seats.

4. The system of claim 1 in which the means for releasably locking includes a ring interior to the shell and groove exterior to the liner receiving said ring therein.

5. The system of claim 1 in which the means for accessing the liner includes slots or castellations at the rim of the shell.

6. The system of claim 1 in which the acetabular cup shell has an exterior surface with nano-springs thereon.

7. The system of claim 1 in which the liner is made of highly cross-linked ultra-high molecular weight polyethylene.

8. The system of claim 1 in which the femoral cap includes an inner surface with nano-springs thereon.

9. The system of claim 1 in which the femoral cap includes an exterior surface with a PVD coating thereon.

10. A veterinary hip resurfacing prosthetic acetabular cup comprising:
  a cross linked ultra-high molecular weight polymer liner having a thickness of less than 2.5 mm;
  a shell receiving the liner therein and having a thickness of less than 2 mm;
  complementary features in the shell and liner preventing rotation of the liner relative to the shell;
  a ring internal to the shell; and
  a groove external to the liner receiving the ring of the shell therein to lock the liner in the shell.

11. The cup of claim 10 in which the shell is approximately 1.0 mm thick and the liner is approximately 1.5 mm thick.

12. The cup of claim 10 in which the complementary features for preventing rotation of the liner relative to the shell includes spaced seats internal in the shell and corresponding spaced tabs exterior to the liner received in said seats.

13. The cup of claim 10 in which further including means for accessing the liner to remove it from the shell.

14. The cup of claim 10 including means for accessing the liner said means including slots or castellations at the rim of the shell.

15. The cup of claim 10 in which the acetabular cup shell has an exterior surface with nano-springs thereon.

* * * * *